(12) United States Patent
Wang et al.

(10) Patent No.: US 8,550,627 B2
(45) Date of Patent: Oct. 8, 2013

(54) PORTABLE FUNDUS OBSERVATION APPARATUS

(75) Inventors: William Wang, Taoyuan (TW); Chung-Cheng Chou, Taoyuan County (TW); Chung-Ping Chuang, Taoyuan (TW); Meng-Shin Yen, Taipei (TW)

(73) Assignee: Crystalvue Medical Corporation, Taoyuan (TW)

( * ) Notice: Subject to any disclaimer, the term of this patent is extended or adjusted under 35 U.S.C. 154(b) by 0 days.

(21) Appl. No.: 13/458,404

(22) Filed: Apr. 27, 2012

(65) Prior Publication Data

US 2012/0274899 A1 Nov. 1, 2012

(30) Foreign Application Priority Data

Apr. 28, 2011 (TW) .............................. 100114817 A

(51) Int. Cl.
*A61B 3/14* (2006.01)
(52) U.S. Cl.
USPC .......................................... 351/206; 351/210

(58) Field of Classification Search
USPC .................................................. 351/200–246
See application file for complete search history.

(56) References Cited

U.S. PATENT DOCUMENTS

| 7,896,496 B2 * | 3/2011 | Hammer et al. ............... 351/206 |
| 8,172,834 B2 * | 5/2012 | Bhadri et al. ..................... 606/2 |
| 8,308,297 B2 * | 11/2012 | Hirose et al. ................... 351/206 |

* cited by examiner

*Primary Examiner* — MOhammed Hasan
(74) *Attorney, Agent, or Firm* — Muncy, Geissler, Olds & Lowe, PLLC

(57) ABSTRACT

A portable fundus observation apparatus includes a body, at least one optical detecting module, and a data processing unit. The body includes a fixing part for fixing the body onto the ocular region of a subject. The optical detecting module includes a light source, an optical lens module, and an image capturing unit. The optical detecting module is separably fixed onto the body. The data processing unit electrically couples with the optical detecting module and processes the fundus image captured by the image capturing unit.

15 Claims, 5 Drawing Sheets

PORTABLE FUNDUS OBSERVATION APPARATUS

BACKGROUND OF THE INVENTION

1. Field of the Invention

The present invention relates to a fundus observation apparatus. In particular, the present invention relates to a portable fundus observation apparatus having a self-observation function.

2. Description of the Prior Art

Eyes are the windows of the soul and play an important role in daily life, hence eyes are essential to everyone. The fundus vessel (retina) is the only part of human vessels that can be observed directly. Systemic diseases, especially the vascular disease, such as glaucoma resulted from diabetic retinopathy, needs regular tracking or primary prevention. Fundus scopes or fundus cameras are often utilized to observe the condition of the eye during the detection and the trace examination to ocular diseases.

The fundus scope mentioned above is easy to use and can make an initial fundus examination. However, the fundus scope has a simplified design and is controlled by one hand to observe one eye at a time. The doctors have to memorize the condition of each eye and the observation result cannot be automatically recorded. As a result, the possibility of misdiagnosis is likely increased and the follow-up tracking is difficult. The deficiencies as mentioned need to be improved.

The fundus camera can provide more detailed and precise detection result; however, in order to achieve the purposes mentioned above, the fundus camera cannot be reduced in weight. As a result, the portability of the fundus camera is poor and the cost is relatively high.

Besides, the fundus detection devices mentioned above are installed at hospitals or health care centers and operated by specialists. As a result, the examination shall be conducted at those places, which consumes lots of time and money, and the test result cannot be provided immediately; it is not convenient for the person who needs a long-term monitoring program.

SUMMARY OF THE INVENTION

It is an object of the present invention to provide an improved fundus observation apparatus which has a self-observation function for a person to perform self-observation and is capable of recording the observation result for the follow-up service. In addition, the fundus observation apparatus of the present invention does not need a massive machine structure, so it is not only portable, cost-reducible, but also suitable for household use and personalization.

To achieve the mentioned object, the present invention provides a portable fundus observation apparatus including a body having a fixing part to fix onto an ocular region of a subject thereby, at least an optical detecting module, and a data processing unit. The optical detecting module includes a light source, an optical lens module, and an image capturing unit. The light source emits light passing through the optical lens module onto fundus of an eye and the image capturing unit utilizes the reflected light to capture an image of the fundus of the eye based on a predetermined focal length. Moreover, the optical detecting module is separably fixed on the body. In other words, the optical detecting module can be secured onto the body or separated from the body. Furthermore, the data processing unit electrically couples to the optical detecting module to transmit the image of the fundus of the eye to the data processing unit, hence the data processing unit may process the image of the fundus of the eye.

To achieve the mentioned object, the present invention provides another portable fundus observation apparatus including a body, at least one optical detecting module, and a signal transmission unit. The body has a fixing part to fix onto an ocular region of a subject. The optical detecting module includes a light source, an optical lens module, and an image capturing unit. After the light source emits light passing through the optical lens module onto fundus of an eye, the image capturing unit utilizes the reflected light to capture an image of the fundus of the eye based on a predetermined focal length. Generally speaking, the optical detecting module is fixed on the body; however, the optical detecting module may be selectively separated from the body. Therefore, the optical detecting module is separably fixed on the body. Besides, the optical detecting module electrically couples to the signal transmission unit to transmit the image of the fundus of the eye by wired or wireless method to an image server for further image recording or image analysis.

DETAILED DESCRIPTION OF THE PREFERRED EMBODIMENT

Embodiments of the present invention will be described in detail with reference to the drawings. In addition, all drawings of the present invention is merely illustrative, not intended to limit the invention to that as described herein; for example, the position of each unit is not limited to the drawings. Throughout this specification the word "this embodiment", "embodiment", or "other embodiment" means a specific quality, structure, or characteristic mentioned in the embodiments of the present invention. Not every phrase "in this embodiment" used in the specification relates to the same embodiment. The terms such as "comparing", "processing", "correcting", "determining", "recording", "commanding" or the like relate to the action or the processing of the computer, computer system, or similar electronic computing device. The computer, computer system, or similar electronic computing device mentioned above controls or changes data of physical (e.g. electronics) quantities stored in the register or the memory of the computer system into other data of physical quantities stored in the memory, register, or other information storage devices of the computer system.

Figure 1:
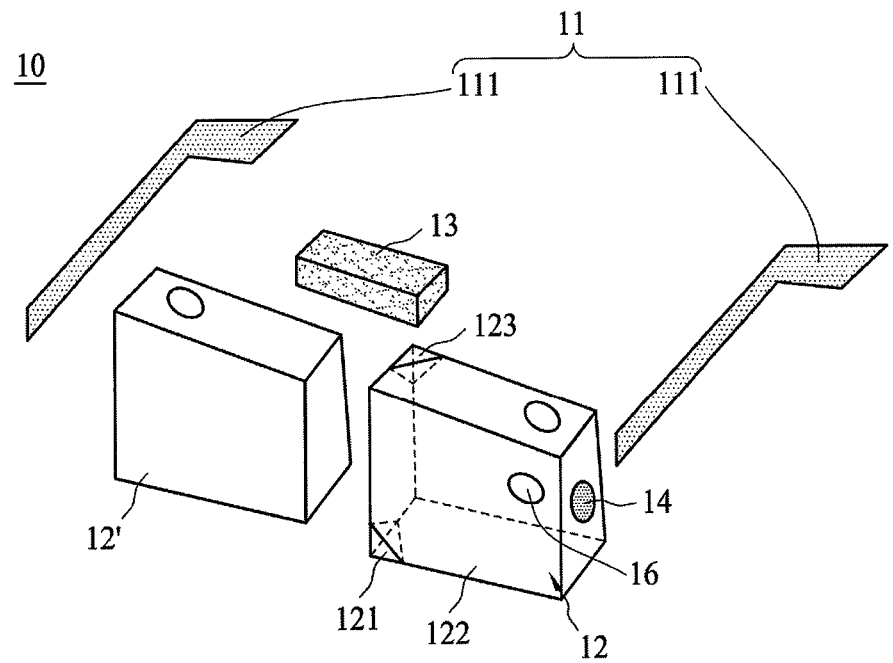
FIG. 1 is an exploded view of one embodiment of the fundus observation apparatus.
Figure 2:
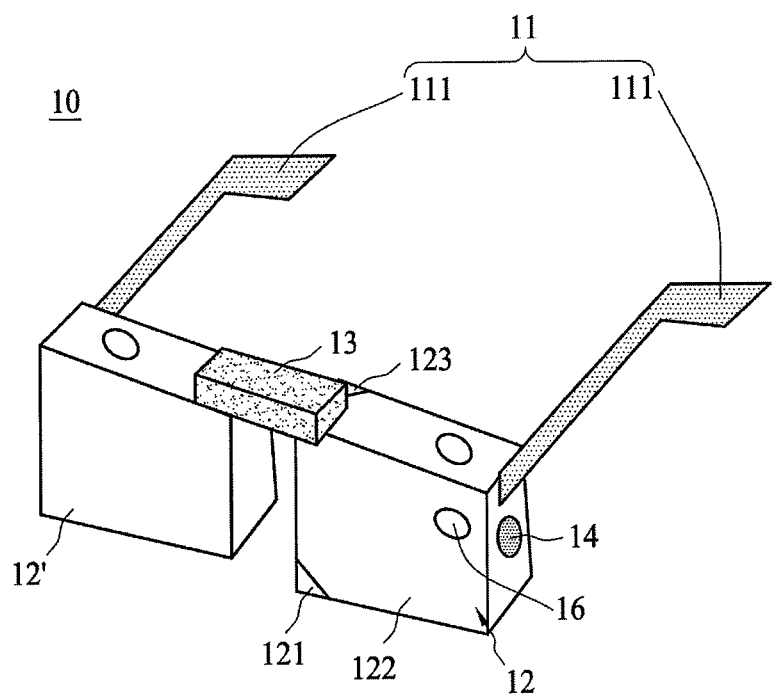
FIG. 2 is a schematic view of the fundus observation apparatus shown in FIG. 1.

Referring to the embodiment of the portable fundus observation apparatus 10 shown in FIG. 1 and FIG. 2, the fundus observation apparatus 10 includes a body 11, at least an optical detecting module 12, and a data processing unit 13. In this embodiment, the body 11 includes two fixing parts 111. In this embodiment, the fixing part 111 is an eyewear frame;

however, in other embodiments, the body 11 may include a single fixing part 111 (such as head band or headgear). The main function of the fixing part 111 is to fix the optical detecting module 12 onto an ocular region of a subject (not shown). However, the fixing part 111 may assist the fixation of the body 11 to further assist the fixation of the optical detecting module 12.

After assembled, the fundus observation apparatus 10 shown in FIG. 1 becomes the fundus observation apparatus 10 shown in FIG. 2. In this embodiment, the fundus observation apparatus 10 includes one optical detecting module 12 fixed onto the ocular region and corresponding to the left eye of the subject by the fixing part 111. As a result, the right eye of the subject may observe the environment normally. The optical detecting module 12 includes a light source 121, an optical lens module 122, and an image capturing unit 123. The light source 121 emits light that passes through the optical lens module 122 onto fundus of an eye of the subject, i.e. the left eye in this embodiment. The image capturing unit 123 captures an image of the fundus of the left eye based on a predetermined focal length (also the best focal length). Since the optical detecting module 12 and the normal lens 12' are easy to detach from the fundus observation apparatus 10, the optical detecting module 12 may be fixed on the body 11 or may detach from the body 11. That is, though the optical detecting module 12 is generally fixed onto the body 11, the optical detecting module 12 can also be easily replaceable to separate from the body 11. As such, it is referred to that the optical detecting module 12 is separably fixed on the body 11. Besides, in other embodiments (not shown), two optical detecting modules 12 can be utilized to detect the left eye and the right eye simultaneously.

As the embodiment mentioned above, the optical detecting module 12 can be easily detached from the body 11. In this embodiment, the optical detecting module 12 and the normal lens 12' are similar in structure, therefore the optical detecting module 12 corresponding to the left eye may be detached to install on the position corresponding to the right eye for further detection on the right eye. As shown in FIG. 2, the data processing unit 13 is disposed on the optical detecting module 12 to connect to the normal lens 12'. Besides, the data processing unit 13 is disposed on one optical detecting module 12 to connect to the other optical detecting module 12 when two optical detecting modules 12 are utilized to detect the left eye and the right eye simultaneously. In this embodiment, the optical detecting module 12 electrically couples to the data processing unit 13, hence, the fundus images of both eyes captured by the image capturing unit 123 of the optical detecting module 12 can be transmitted to the data processing unit 13 to process the images of the fundus of eye. The processing described herein includes recoding the images of the fundus of the eye and correcting the images of the fundus of the eye based on the reflected light from the fundus of the eye received by the optical detecting module 12. As such, the failing of comparing the images of the fundus of the eye captured by different optical detecting modules 12 can be avoided, and the ability of the follow-up tracking is provided to improve the accuracy of diagnosis.

In the embodiment shown in FIG. 1 and FIG. 2, the fundus observation apparatus 10 further includes a control unit 14. In this embodiment, the control unit 14 is disposed on the optical detecting module 12. As shown in FIG. 1 and FIG. 2, the optical detecting module 12 has an inner surface and a side surface. The inner surface faces the ocular region of the subject, and the control unit 14 is preferably disposed on the side surface. In other embodiments (not shown), the control unit 14 may adopt different designs to be disposed on the body 11, the fixing part 111, or the data processing unit 13. The control unit 14 is operated by the subject for optical focusing, target confirming, or the image capturing of the fundus of the eye or by the professional health care personnel for the procedures mentioned above. In addition to the functions mentioned above, the control unit 14 can adjust the focus of the optical detecting module 12. When the control unit 14 adjusts the focus to the predetermined focal length (also the best focal length), the data processing unit 13 provides an image signal, an audio signal, or a flashing signal to alert the subject or the professional health care personnel that the predetermined focal length is reached or alert the subject or the professional health care personnel that the image of the fundus of the eye has been captured under the predetermined focal length. In other embodiments (not shown), the control unit 14 may be omitted if the optical detecting module 12 can automatically adjust the focus to the predetermined focal length for capturing the image of the fundus of the eye.

Figure 3:
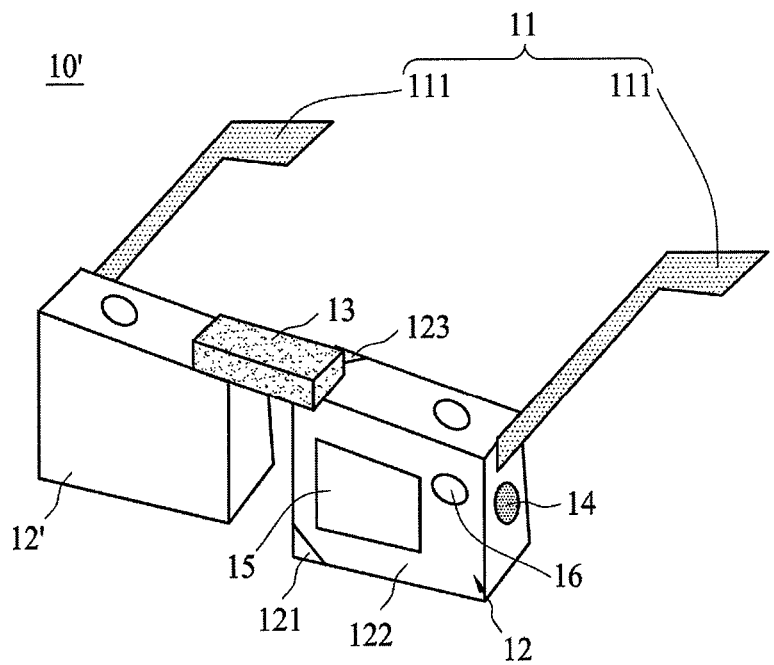
FIG. 3 is a schematic view of another embodiment of the fundus observation apparatus.

In another embodiment shown in FIG. 3, the fundus observation apparatus 10' further includes a display unit 15. In this embodiment, the display unit 15 is disposed on the back side (opposite to the left eye) of the optical detecting module 12. The display unit 15 may also be disposed on the body 11 or the data processing unit 13 according to different design requirements. In this embodiment, the display unit 15 electrically couples the optical detecting module 12, so that the display unit 15 can immediately display the image of the fundus of the eye captured by the optical detecting module 12 to allow the professional health care personnel to immediately observe and interpret the desired fundus region of the eye further to track the specific region of interest.

Figure 4:
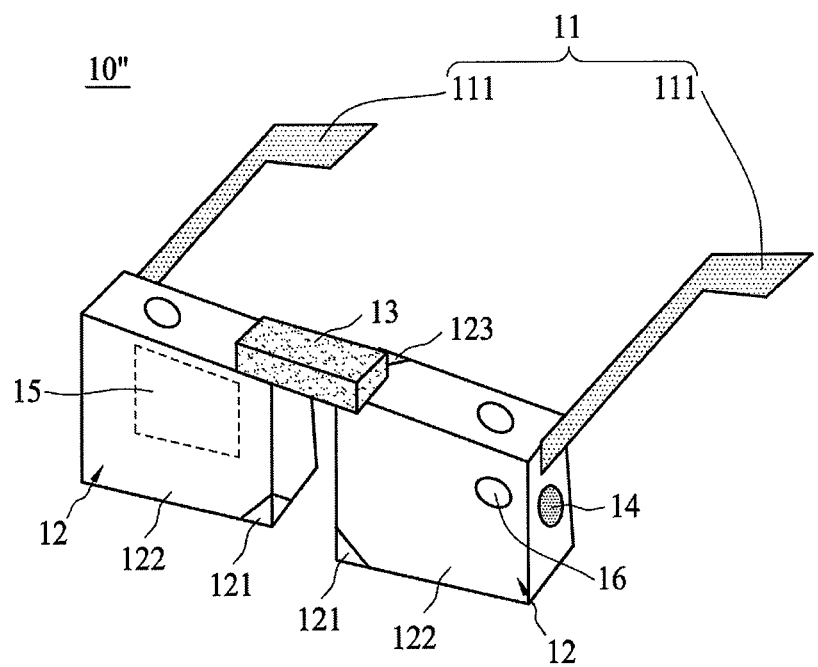
FIG. 4 is a schematic view of another embodiment of the fundus observation apparatus.

In another embodiment of the fundus observation apparatus 10" shown in FIG. 4, the display unit 15 can directly display the image of the fundus of the left eye to the right eye for observation by the subject. Besides, since the data processing unit 13 electrically couples the display unit 15 of the optical detecting module 12, the image of the fundus of the eye recorded previously can be provided for the subject to make an initial comparison or to track the desired fundus region of the eye. In addition, the fundus observation apparatus 10" of this embodiment may also include a control unit 14. When the control unit 14 adjusts the focus to the predetermined focal length, the display unit 15 provides a flashing signal or an image signal to alert the subject for determination whether to capture the image of the fundus of the eye of not.

The fundus observation apparatus 10, 10', or 10" shown in FIG. 1 to FIG. 4 further includes an alert unit 16 disposed on a front surface of the optical detecting module 12. The front surface is opposite to the inner surface which faces the ocular region of the subject, wherein when the optical detecting module 12 reaches the predetermined focal length, the alert unit 16 provides an audio signal to alert the subject or professional health care personnel.

Figure 5:
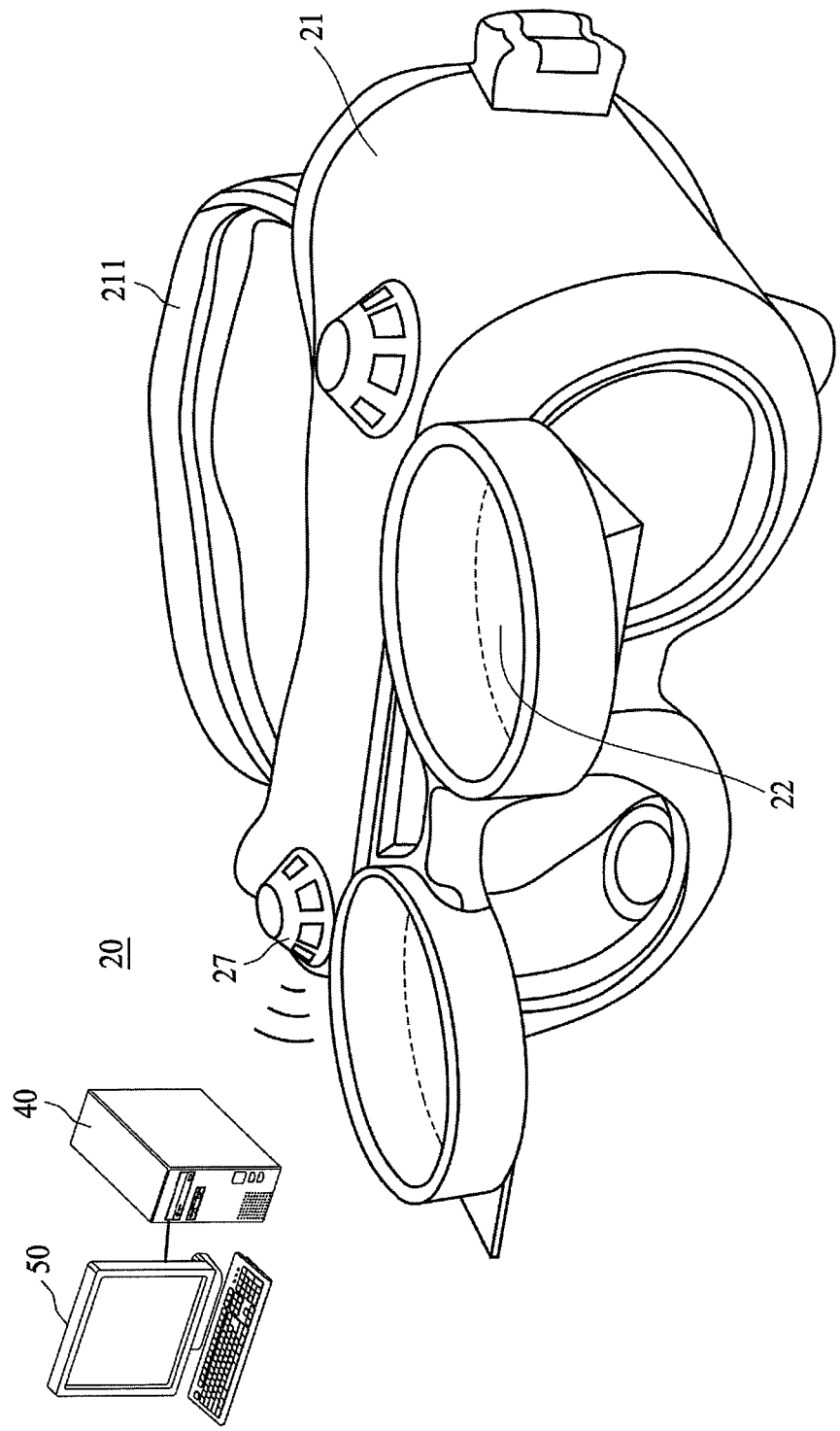
FIG. 5 is a schematic view of another embodiment of the fundus observation apparatus.

In the embodiment of the fundus observation apparatus 20 shown in the FIG. 5, the fundus observation apparatus 20 includes a body 21, at least one optical detecting module 22, and a signal transmission unit 27. In this embodiment, the body 21 has a fixing part 211. The fixing part 211 is a head band.

Figure 6:
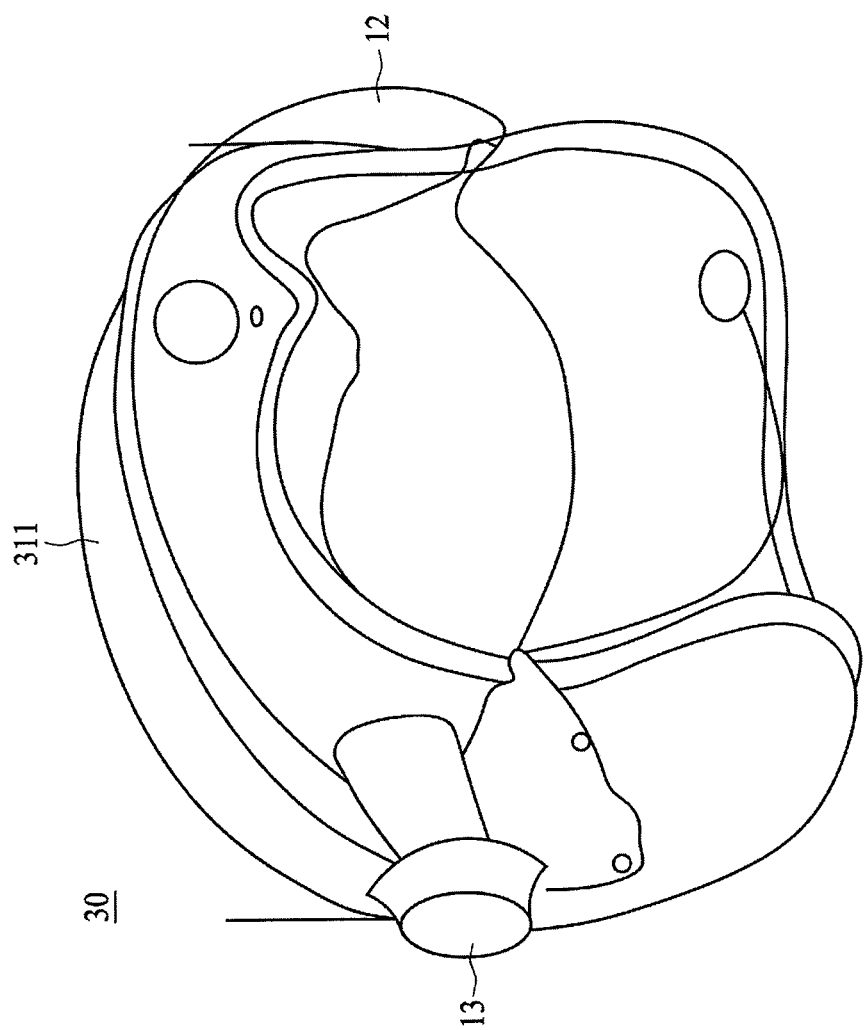
FIG. 6 is a schematic view of another embodiment of the fundus observation apparatus.

In the embodiment shown in the FIG. 6, the fixing part 311 of the fundus observation apparatus 30 is a helmet or other fixing parts which can provide a similar function. In the embodiment shown in the FIG. 5, the body 21 is fixed onto the ocular region of the subject (not shown) by the fixing part 211 and the optical detecting module 22 is fixed indirectly onto the ocular region. In this embodiment, the body 21 of the fundus observation apparatus 20 is configured as a telescope body and the optical detecting module 22 is configured as a lens that can be liftably disposed on the body 21 as shown in FIG. 5. Because the optical detecting module 22 is replaceable easily due to such a configuration, it can be designed as a monocular optical detecting module 22 mentioned above or as a binocular optical detecting module 22. The optical detecting module 22 includes a light source (not shown), a optical lens module (not shown), and an image capturing unit (not shown) as those described above; the composition and the function of these elements can be referred to the previous embodiment and will not be elaborated hereinafter. In this embodiment, the optical detecting module 22 is separably fixed on the body 21, i.e. the optical detecting module 22 is lifted (moved away from the body 21) or is not lifted (moved close to the body 21 to form a telescope with the body 21).

In the embodiment of the fundus observation apparatus 20 shown in the FIG. 5, the signal transmission unit 27 is disposed on the body 21; however, in other embodiments (not shown), the signal transmission unit 27 may be disposed on the optical detecting module 22. In this embodiment, the signal transmission unit 27 electrically couples to the optical detecting module 22. As a result, the signal transmission unit 27 can output the image of the fundus of the eye to an image server 40 in a wireless or non-wireless manner and then the image server 40 can record and analyze the image of the fundus of the eye remotely. Preferably, the signal transmission unit 27 wirelessly transmits images of the fundus of eyes to the image server 40 for remote processing. Besides, the fundus observation apparatus 20 further includes a display device 50 electrically coupling to the image server 40. As such, the display device 50 can display the image of the fundus of the eye recorded by the image server 40 and the professional health care personnel can remotely diagnose and interpret whether the subject needs to be in the hospital. In addition, when one eye (such as the left eye) is under detection, the subject can observe the image of the fundus of the left eye displayed by the display device 50 through the other eye (such as the right eye) to determine and track the desired fundus region of the left eye.

Figure 7:
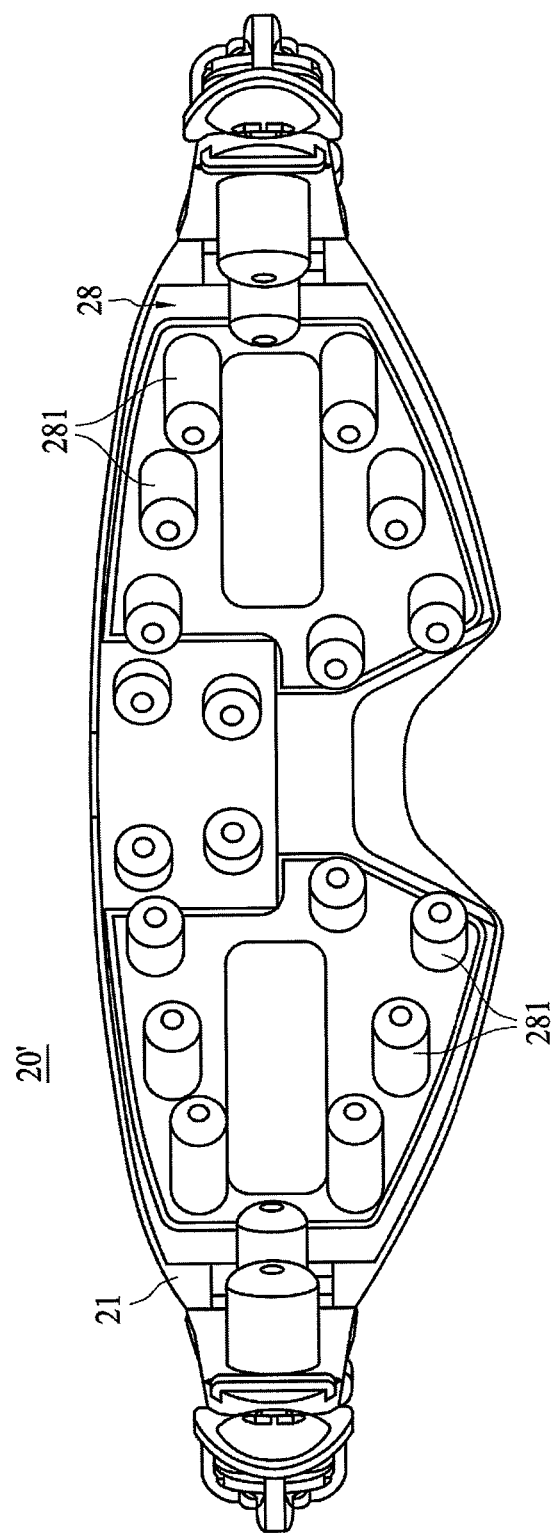
FIG. 7 is a schematic view of another embodiment of the fundus observation apparatus.

In addition, in the embodiment shown in FIG. 7, the fundus observation apparatus 20' further includes an eye fixing mechanism 28 disposed on one side of the body 21 facing the eye of the subject (not shown). The eye fixing mechanism 28 includes a plurality of posts for pushing and fixing an eyelid (not shown) of the eye to prevent the eyelid from moving during self detection or prevent the observation difficulty induced by the movement of the eye.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A portable fundus observation apparatus, comprising:
   a body including a fixing part;
   at least an optical detecting module including a light source, an optical lens module, and an image capturing unit, wherein the light source emits light passing through the optical lens module onto fundus of an eye, the image capturing unit captures an image of the fundus of the eye based on a predetermined focal length, the optical detecting module is separably fixed on the body; and
   a data processing unit electrically coupling to the optical detecting module and processing the image of the fundus of the eye, wherein the data processing unit and the optical detecting module are physically integrated to be fixed onto an ocular region of a subject by wearing the fixing part.

2. The portable fundus observation apparatus of claim 1, further comprising a display unit disposed on a back side of the optical detecting module, wherein the display unit displays the image of the fundus of the eye to the other eye of the subject for the subject's observation.

3. The portable fundus observation apparatus of claim 1, wherein the data processing unit is disposed on the optical detecting module to connect to a normal lens or another optical detecting module, and the data processing unit provides an image signal, an audio signal, or a flashing signal to alert the subject that the predetermined focal length is reached.

4. The portable fundus observation apparatus of claim 2, further comprising a control unit for adjusting a focus of the optical detecting module, wherein the optical detecting module has an inner surface and a side surface, the inner surface faces the ocular region of the subject, the control unit is disposed on the side surface, when the control unit adjusts the focus to the predetermined focal length, the display unit provides a flashing signal or an image signal to alert the subject.

5. The portable fundus observation apparatus of claim 1, further comprising an alert unit, wherein the optical detecting module has an inner surface and a front surface opposite to the inner surface, the inner surface faces the ocular region of the subject, the alert unit is disposed on the front surface, when the optical detecting module reaches the predetermined focal length, the alert unit provides an audio signal to alert the subject.

6. The portable fundus observation apparatus of claim 1, further comprising an eye fixing mechanism disposed on one side of the body facing the eye of the subject, wherein the eye fixing mechanism comprises a plurality of posts for pushing and fixing an eyelid of the eye.

7. The portable fundus observation apparatus of claim 1, wherein the fixing part is selected from a head band, an eyewear frame, and a helmet.

8. A portable fundus observation apparatus, comprising:
   a body including a fixing part;
   at least an optical detecting module including a light source, an optical lens module, and an image capturing unit, wherein the light source emits light passing through the optical lens module onto fundus of an eye, the image capturing unit captures an image of the fundus of the eye based on a predetermined focal length, the optical detecting module is separably fixed on the body; and
   a signal transmission unit electrically coupling to the optical detecting module and outputting the image of the fundus of the eye to an image server, wherein the signal transmission unit and the optical detecting module are physically integrated to be fixed onto an ocular region of a subject by wearing the fixing part.

9. The portable fundus observation apparatus of claim 8, further comprising a display unit disposed on a back side of the optical detecting module, wherein the display unit displays the image of the fundus of the eye to the other eye of the subject for the subject's observation.

10. The portable fundus observation apparatus of claim 9, further comprising a control unit for adjusting a focus of the optical detecting module, wherein the optical detecting module has an inner surface and a side surface, the inner surface faces the ocular region of the subject, the control unit is disposed on the side surface, when the control unit adjusts the focus to the predetermined focal length, the display unit provides a flashing signal or an image signal to alert the subject.

11. The portable fundus observation apparatus of claim 8, further comprising an alert unit, wherein the optical detecting module has an inner surface and a front surface opposite to the inner surface, the inner surface faces the ocular region of the subject, the alert unit is disposed on the front surface, when the optical detecting module reaches the predetermined focal length, the alert unit provides an audio signal to alert the subject.

12. The portable fundus observation apparatus of claim 8, further comprising an eye fixing mechanism disposed on one side of the body facing the eye of the subject, wherein the eye fixing mechanism comprises a plurality of posts for pushing and fixing an eyelid of the eye.

13. The portable fundus observation apparatus of claim 8, wherein the fixing part is selected from a head band, an eyewear frame, and a helmet.

14. The portable fundus observation apparatus of claim 8, further comprising a display device electrically coupling to the image server and providing the image of the fundus of the eye.

15. The portable fundus observation apparatus of claim 14, wherein the display device displays the image of the fundus of the eye to the other eye of the subject for the subject's observation.

\* \* \* \* \*